United States Patent [19]
Lee et al.

[11] Patent Number: 4,697,026
[45] Date of Patent: Sep. 29, 1987

[54] ACRYL FUNCTIONAL SILICONE COMPOUNDS

[75] Inventors: Chi-long Lee; Michael A. Lutz, both of Midland, Mich.

[73] Assignee: Dow Corning Corporation, Midland, Mich.

[21] Appl. No.: 816,477

[22] Filed: Jan. 6, 1986

[51] Int. Cl.$^4$ ................................................ C07F 7/10
[52] U.S. Cl. .................................... 556/418; 556/419; 556/414; 556/424; 556/420; 556/425; 556/423; 556/413; 522/99; 260/404; 260/404.5; 528/26; 528/33; 528/41; 525/479
[58] Field of Search ............... 556/418, 419, 414, 424, 556/420, 425, 423, 413; 260/404, 404.5

[56] References Cited
U.S. PATENT DOCUMENTS

| | | | |
|---|---|---|---|
| 4,201,808 | 5/1980 | Cully et al. | 428/40 |
| 4,209,455 | 6/1980 | Pepe | 556/418 X |
| 4,260,780 | 4/1981 | West | 556/430 |
| 4,276,402 | 6/1981 | Chromecek et al. | 556/419 X |
| 4,276,424 | 6/1981 | Peterson et al. | 556/430 |
| 4,293,397 | 10/1981 | Sato | 204/159.13 |
| 4,314,956 | 2/1982 | Baney et al. | 264/65 |
| 4,324,910 | 4/1982 | West et al. | 556/430 |
| 4,348,454 | 9/1982 | Eckberg | 428/334 |
| 4,554,369 | 11/1985 | Hill et al. | 556/418 |

Primary Examiner—Paul F. Shaver
Attorney, Agent, or Firm—Roger H. Borrousch

[57] ABSTRACT

Acryl functional silicone compounds are made by reacting an amine functional silicon compound with a di- or multi-functional acryl compound by a Michael-type addition reaction. These acryl functional silicone compounds are purer than others because no catalyst is used and no by-products are formed. These acryl functional silicone compounds can be used as adhesion promoters and as coating compositions which can be cured by ultraviolet radiation.

26 Claims, No Drawings

ACRYL FUNCTIONAL SILICONE COMPOUNDS

BACKGROUND OF THE INVENTION

1. Field of the Invention

This invention relates to acryl functional silicone compounds and to a method of preparing them.

2. Background Information

Silicone compounds which contain an acryl function are known in the art. These compounds can be acrylate, methacrylate, acrylamide, and methacrylamide. When the silicone compounds are polymeric, the known methods of preparation produce product which contains catalyst residue and other by-products of the reaction. These residues and by-products can be undesirable, especially for certain applications. One approach to overcome this problem is to remove these unwanted materials, however removal of these materials can be very difficult and expensive. Therefore a method of preparing an acryl functional silicone compound which did not produce catalyst residue or other-by-products would be a very desirable method and the resultant acryl functional silicone compounds would be purer than previously achieved directly from a process of preparation.

One method of preparing the acryl functional silicone compounds is to react a hydroxyalkylacrylate with a chlorosilicon to produce the acryl functional silicone compound with HCl as a by-product. The reaction can be run in the presence of an acid acceptor, such as an amine which makes an amine hydrochloride salt, or it can be run under partial vacuum to remove the HCl by-product, as it is formed. The amine hydrochloride salt is very difficult to remove and thus cost is high. The use of a partial vacuum to remove the gaseous HCl is also expensive. A method of making acryl functional silicone polymers by using an amine acid acceptor is described by Eckberg in U.S. Pat. No. 4,348,454, issued Sept. 7, 1982. Cully et al. in U.S. Pat. No. 4,201,808, issued May 6, 1980 describes a method of using partial vacuum to remove the HCl for the reaction of a hydroxyalkylacrylate with a chlorosilicon to produce an acryl functional silicone polymer.

Sato et al. in U.S. Pat. No. 4,293,397, issued Oct. 6, 1981, teach that an acryl functional silicone polymer can be made by reacting an amino-terminated diorganopolysiloxane with glycidyl acrylate or glycidyl methacrylate in an inert atmosphere, such as nitrogen, at temperatures of 50° to 70° C. for 6 to 96 hours having a polymerization inhibitor present, such as hydroquinone monomethyl ether, to prevent thermal polymerization of the acrylic acid derivative. The reaction product is a siloxane with groups of the following formula

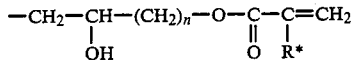

in which R* is hydrogen or an alkyl group of one to four carbon atoms. In view of this Sato et al. patent, the present invention was unexpected, because the acryl functional compounds of the Sato et al. patent which react with the amino-functional silicone polymer, react through the glycidyl functional group and the acryl group remains unreacted. In view of the other art and Sato et al., the reaction between the acryl functional compounds and the amino functional silicon compound would not be expected to go without a catalyst or the reaction would require conditions which would be too harsh for the acryl functional group to survive.

SUMMARY OF THE INVENTION

The present invention relates to acryl functional silicon compounds which can be prepared without generating catalyst residues or reaction by-products and can be cured by radiation, such as ultraviolet radiation.

The present invention relates to an acryl functional silicone compound consisting essentially of at least one silicon atom having an acryl functional radical bonded to the silicon atom through a silicon-carbon bond, where the acryl functional radical contains at least one carbon-nitrogen-carbon bond and an acrylate, methacrylate, acrylamide, or methacrylamide group, any other groups bonded to the silicon atom being monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together, and silicon atoms which are present and which do not have an acryl functional radical bonded thereto can have bonded thereto monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together.

This invention also relates to a method of preparing an acryl functional silicone compound comprising forming an intimate mixture of an amino functional silicon compound in which the amino group is a primary amine or a secondary amine and an acryl functional compound having at least two acrylate, methacrylate, acrylamide, or methacrylamide groups per molecule at a temperature less than 100° C. for a time sufficient to produce an acryl functional silicone compound in which at least one silicon atom has an acryl functional radical bonded to the silicon atom through a silicon-carbon bond, where the acryl functional radical contains at least one carbon-nitrogen-carbon bond and an acrylate, methacrylate, acrylamide, or methacrylamide group, any other groups bonded to the silicon atom being monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together, and silicon atoms which are present and which do not have an acryl functional radical bonded thereto can have bonded thereto monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together.

DESCRIPTION OF THE PREFERRED EMBODIMENTS

The acryl functional silicon compounds of this invention can be prepared by intimately mixing an amino functional silicon compound having at least one primary amine or secondary amine group with an acryl functional compound having at least two acrylate, methacrylate, acrylamide, or methacrylamide groups per molecule. For purposes of this invention, the term "acryl functional" or "acryl functionality" refers to the following groups: acrylate ($CH_2$=CHCOOC—), methacrylate [$CH_2$=C($CH_3$)COOC—], acrylamide ($CH_2$=CHCONHC—), and methacrylamide [$CH_2$=C($CH_3$)CONHC—]. When amine compound and acryl compound are mixed, there is a reaction which produces an acryl functional silicon compound. This reaction is known as the Michael-type addition reaction. This reaction occurs at room temperature but is rather slow for many commercial applications, for example the reaction may take as long as 24 hours or more to convert only 40% of the amine to the acryl functionality.

Heating the mixture increases the rate of the reaction and at 70° C. as much as 80% of the amine can be converted to the acryl functionality. The mixture should not be heated above 100° C. because temperatures above 100° C. can cause considerable loss of the acryl functionality due to a free radical initiated chain reaction. Free radical scavengers, such as p-methoxyphenol, are useful to inhibit the unwanted chain reaction, but these scavengers also inhibit the reactivity of the final acryl functional silicone compound during its use unless they are removed. Although free radical scavengers can be used, their use would add expense to making improved purity acryl functional silicone compounds.

If the intimate mixture is formed in a solvent, the reaction rate may increase slightly, such as in a 24 hour period at room temperature up to 45 to 50% of the amine may be converted to the acryl functionality. Solvents referred to are those which are commonly used for silicone reactions such as toluene, xylene, benzene, hexane, pentane, mineral spirits, trimethylsiloxy endblocked polydimethylsiloxane, and cyclopolydimethylsiloxane. Many of these solvents have high boiling points, are difficult to remove from the acryl functional silicone compounds produced, have environmentally undesirable properties, and are hazardous to use. Thus besides providing low conversion, these solvents have other undesirable properties.

The best reaction conditions are those in which the intimate mixture is formed using a promoter solvent, such as an alcohol. The preferred alcohols are those which can readily be removed from the reaction product without having to heat it to too high of a temperature. Examples of promoter alcohols are ethanol and isopropanol. The use of the promoter solvent can increase the rate of the reaction such that 90 to 95% of the amine is converted to the acryl functionality. The fastest reactions would be those using a promoter solvent and heating the mixture to a temperature above 25° C. and below 100° C.

Any of the above reactions can be used to make the acryl functional silicone compounds of this invention. Although some of the methods use solvents, the resulting products are purer than those reactions which use amines to form salts of the by-produced acid. These methods offer the advantage that the silicone compound can be prepared in the desired structural form before the acryl functionality is in place on the molecule. The amine functional silicon compounds can withstand the higher temperatures of preparation while the acryl functionality cannot. For example, the preparation of poly(co-diphenylsiloxane-co-dimethylsiloxane) requires an alkaline equilibration catalyst with heating to high temperatures, such as 150° C., of a mixture of cyclopolydimethylsiloxane and cyclopolydiphenylsiloxane. The preparation of a polymer having dimethylsiloxane units, diphenylsiloxane units, and siloxane units having acryl functionality could not survive the reaction without causing the acryl functionality to polymerize and thus an acryl functional silicone compound of this type could not produced. However, the method of this invention can be used to prepare such compounds. For example, the mixture of the cyclopolydimethylsiloxane, the cyclopolydiphenylsiloxane, the alkaline equilibration catalyst, and an amine bearing siloxane precursor could be used to make an amine functional poly(co-diphenylsiloxane-co-dimethylsiloxane) which could then be converted into an acryl functional siloxane compound at lower temperatures by the method of this invention. The amine functionality can survive such reactions much more readily than the acryl functionality. The amine functionality can survive even more severe conditions, therefore the method of this invention is an attractive route to acryl functional silicone compounds.

The amine functionality can be either primary or secondary. The primary amine functionality reacts much more readily than the secondary amine functionality. For this reason, the multi-functional acryl compound used to react with the amine react readily with the primary amine and the additional acryl functional groups do not readily react. Such a difference in reaction rates between the primary and secondary amines can be used to advantage in the method of this invention. After one of the acryl groups of the multi-functional compound reacts with the primary amine, the reaction can be stopped by adding monofunctional acryl compounds to react with the remaining secondary amine hydrogens. This method can be used to prepare acryl functional silicone compounds which have larger amounts of acryl groups but retain shelf stability and also can be used to make compounds which have a desired amount of acryl groups.

The reaction between the amine functional silicon compound and the multi-functional acryl compound can be stopped by adding a monofunctional acryl compound to the reaction mixture. The monofunctional acryl compound can be added at two points during the reaction. The amine functional silicon compound and the multi-functional acryl compound can be mixed and at the point one wishes the reaction stopped, the monofunctional acryl compound is added. One could also add the monofunctional acryl compound at the beginning of the reaction, but this uses up amine hydrogen atoms, especially primary amine hydrogen atoms. The monofunctional acryl compound is preferably added after the reaction has begun so that the monofunctional acryl compounds do not compete with the multi-functional acryl compounds in such a manner that the number of acryl groups on the final silicon compound is not the desired product.

The reaction can also be stopped by another method in which the reaction between the multi-functional acryl compound and the amine functional silicon compound is stopped by adding an acid anhydride. Using the acid anhydride to stop the reaction, has the same benefits as using a monofunctional acryl compound with respects to shelf stability, but the use of the acid anhydride has the added advantage that a new compound is formed, namely one in which the acryl functional silicone compound has the following group

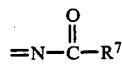

wherein $R^7$ is a monovalent hydrocarbon radical or a radical of the general formula $-R^8-COOH$ in which $R^8$ is a divalent hydrocarbon radical.

The amounts of amine functional silicon compound and the acryl functional compound should be such that there is at least one molecule of acryl functional compound per primary amine hydrogen. It should be understood that the amounts of the amine functional silicon compound and the acryl functional compound can be such that there is less than one molecule of acryl functional compound per primary amine hydrogen, but in such instances precautions should be taken to ensure adequate shelf life for the reaction product. The acryl functional silicone compounds made with less than one molecule of acryl functional compound per primary amine hydrogen may contain crosslinking as a result of two or more of the acryl functional groups on one acryl functional compound reacting with primary amine hydrogen atoms on different amine functional silicone compounds. When two acryl functional groups on one molecule react with two hydrogen atoms of primary amine groups on different amine functional silicon compounds, the product can gel before it is put to use. The foregoing ratio of acryl functional compound to primary amine hydrogen does not mean that the secondary amine hydrogen atoms do not react but only that they react slower and can be readily stopped from reacting by the above mentioned methods.

The amine functional silicon compounds used in the method of this invention can be any of those known in the art which have primary and secondary amine functionality. These compounds can be prepared by methods well-known in the art and many are commercially available.

Amine functional silanes can be exemplified by the following general formula

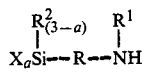

wherein

R is a divalent hydrocarbon radical or a divalent hydrocarbon radical having amino functionality of the formula $=NH$ in which the two bonds of the $=NH$ are bonded to carbon atoms, $R^1$ is hydrogen or an alkyl radical having from 1 to 4 carbon atoms per radical, such as methyl, ethyl, propyl, isopropyl, butyl, and isobutyl, $R^2$ is a monovalent hydrocarbon radical or fluorinated alkyl radical, X is a hydrolyzable group whose hydrolyzed groups do not form salts with the nitrogen atom, and a is 1, 2, or 3.

Examples of R are divalent hydrocarbon radicals, such as methylene, ethylene, butylene, hexylene, propylene, decylene,

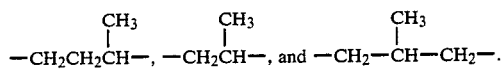

R can also be a divalent hydrocarbon radical having amino functionality of the formula $=NH$ in which the two bonds of the $=NH$ are bonded to carbon atoms, such radicals are illustrated by $-CH_2CH_2CH_2-NH-CH_2CH_2-$, $-CH_2CH_2CH_2-(NH-CH_2CH_2)_2-$, $-CH_2CH_2CH_2-(NH-CH_2CH_2)_3-$, and $-CH_2CH_2CH_2-(NH-CH_2CH_2)_4-$. $R^2$ can be illustrated by methyl, ethyl, propyl, butyl, phenyl, octadecyl, 2-phenylethyl, vinyl, 3,3,3-trifluoropropyl, 2-(perfluoroethyl)ethyl, and 2-(perfluorobutyl)ethyl. X is illustrated by an alkoxy radical or an N,N-dialkylamino radical. Examples of alkoxy radical are methoxy, ethoxy, propoxy, butoxy, 2-ethylhexoxy, isopropoxy, hexyloxy, 2-methoxyethoxy, 2-ethoxyethoxy. Examples of N,N-dialkylamino radicals are dimethylamino, diethylamino, and diisopropylamino. Examples of such silanes are gamma-aminopropyltriethoxysilane, gamma-aminopropylmethyldiethoxysilane, gamma-aminopropylethyldiethoxysilane, gamma-aminopropylphenyldiethoxysilane, delta-aminobutyltriethoxysilane, delta-aminobutylmethyldiethoxysilane, delta-aminobutylethyldiethoxysilane, delta-aminobutylphenyldiethoxysilane, gamma-aminoisobutylmethyldimethoxysilane, aminomethyltrimethoxysilane, gamma-aminopropyltrimethoxysilane, N-methyl-gamma-aminopropyltrimethoxysilane, gamma-aminopropyltripropoxysilane, gamma-aminopropyltri(methoxyethoxy)silane, beta-aminoethyltriethoxysilane, gamma-aminobutyltriethoxysilane, N-methyl-gamma-aminopropylmethyldibutoxysilane, delta-aminobutyltrimethoxysilane, delta-aminobutyldimethylmethoxysilane, beta-aminopropyltriethoxysilane, $(CH_3O)_3SiCH_2CH_2CH_2NHCH_2CH_2NH_2$, $(CH_3O)_3SiCH_2CH_2CH_2(NHCH_2CH_2)_2NH_2$, $(CH_3O)_3SiCH_2CH_2CH_2(NHCH_2CH_2)_3NH_2$, $(C_2H_5O)_3SiCH_2CH_2CH_2(NHCH_2CH_2)_4NH_2$, N-butyl-gamma-aminopropyltrimethoxysilane, and N-methyl-beta-aminopropyltriethoxysilane. Example of N,N-dialkylamino silanes are gamma-aminopropyltris(N,N-dimethylamino)silane, gamma-aminopropyltris(N,N-diethylamino)silane, and

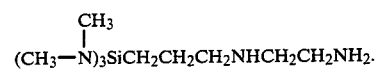

The silanes described above can be hydrolyzed in any combination to provide amine functional silicon compounds which can be used in the method of this invention to make acryl functional silicon compounds. These silanes can also be hydrolyzed with other silanes which do not contain amine functionality to make still other amine functional silicon compounds for use in the method of this invention.

The hydrolyzed silanes described above and siloxanes made by equilibrating cyclic siloxanes can make amine functional siloxanes which can be used in the method of this invention to make the acryl functional silicon compounds. These amine functional siloxanes have a general average unit formula

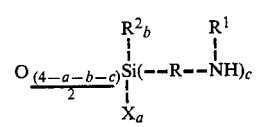

in which R, $R^1$, $R^2$, and X are the same as defined above, a has an average value of $<3$, b has an average value of $<3$, c has an average value such that there is at least one —R—NHR[1] radical per molecule of amine functional siloxane, and the sum of a+b+c is <4.

A preferred amine functional siloxane for this invention has the following formula

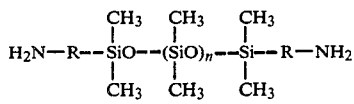

in which R is defined above and n has an average value of zero or greater, preferably 10 to 300. Other preferred amine functional siloxanes for this invention are those having the following general formula

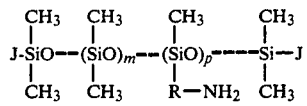

in which R is defined above; J is either methyl or —R—NH$_2$, preferably methyl; m has an average value of zero or greater, preferably 100 to 500; and p has an average value of at least one, preferably 2 to 20.

The multi-functional acryl compounds used in this invention are available commercially or can be made by well-known methods. Examples of the difunctional acryl compounds are the diacrylates, including 1,6-hexanediol diacrylate, 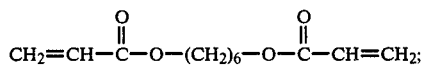

1,4-butanediol diacrylate, 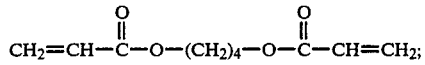

ethylene glycol diacrylate, 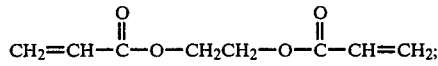

diethylene glycol diacrylate, 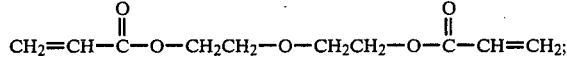

tetraethylene glycol diacrylate, 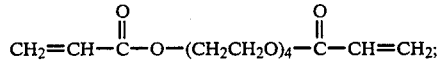

tripropylene glycol diacrylate, 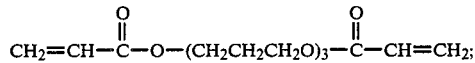

neopentyl glycol diacrylate, 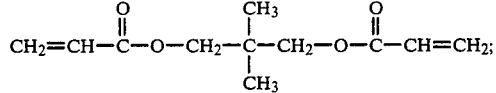

1,4-butanediol dimethacrylate, 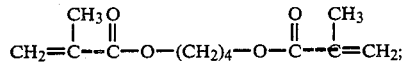

poly(butanediol) diacrylate, 

tetraethylene glycol dimethacrylate, 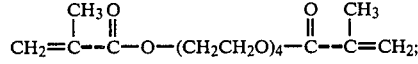

1,3-butylene glycol diacrylate, 

triethylene glycol diacrylate, 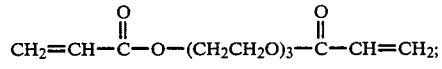

triisopropylene glycol diacrylate, 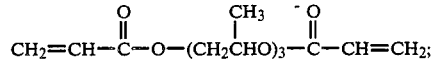

polyethylene glycol diacrylate, 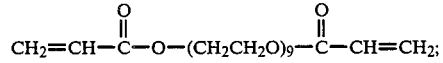

ethoxylated bisphenol A diacrylate,

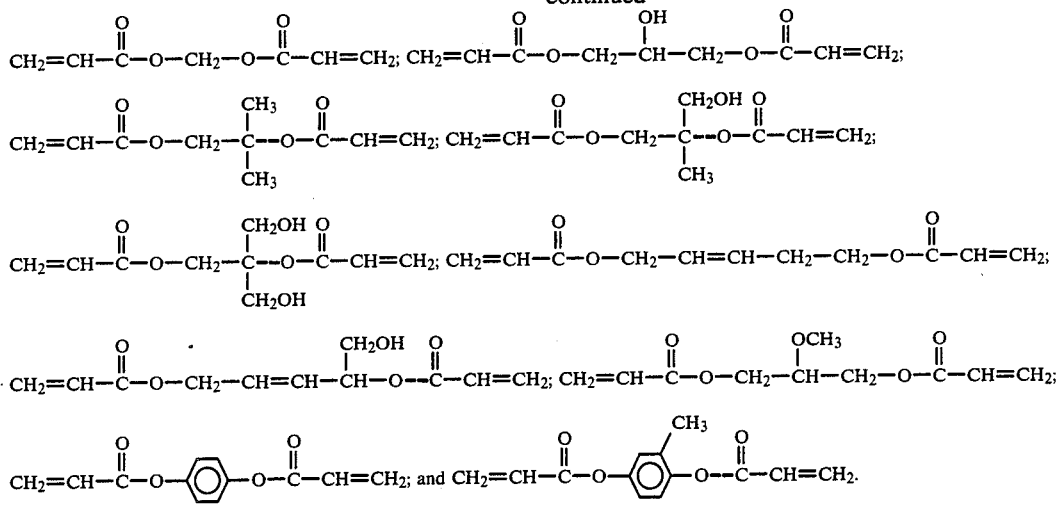

Examples of acrylates which have three of more acrylate groups include trimethylolpropane triacrylate,
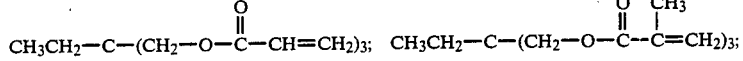

trimethylolpropane trimethacrylate,
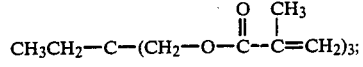

pentaerythritol monohydroxy triacrylate, pentaerythritol tetraacrylate,
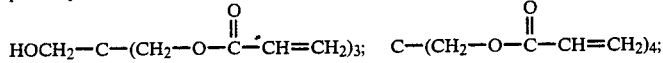

dipentaerythritol (monohydroxy) pentaacrylate,
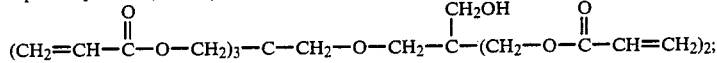

trimethylolpropane triethoxy triacrylate,
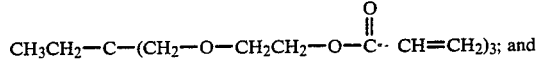

and di-trimethylolpropane tetraacrylate,
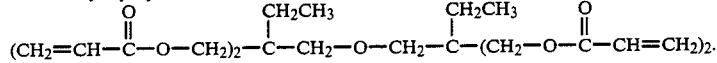

Examples of acrylamide compounds include

N,N'—hexamethylene-bis-methacrylamide,
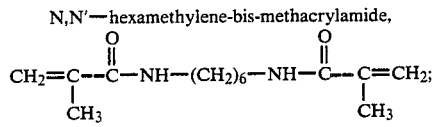

N,N'—isovalerylidene-bis-methacrylamide,
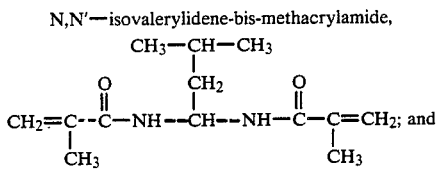

N,N'—methylene-bis-methacrylamide,
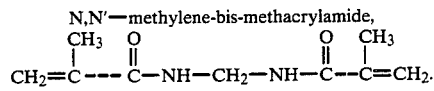

The monofunctional acryl compounds used to stop the reaction between the multi-functional acryl compound and the amine functional silicon compound can be illustrated by ethylhexyl acrylate, isobornyl acrylate, methyl methacrylate, n-butyl acrylate, ethyl acrylate, methyl acrylate, N,N'-dimethyl acrylamide, and ethyl methacrylate.

The anhydrides which can be used to stop the reaction and also produce new compounds can be illustrated by acrylic anhydride, acetic anhydride, propionic anhydride, butyric anhydride, isovaleric anhydride, caproic anhydride, palmitic anhydride, stearic anhydride, succinic anhydride, and glutaric anhydride. Acryl functional silicon compounds which are prepared using the anhydride can exhibit suitable release characteristics for use in making paper coating compositions.

The acryl functional silicon compounds of this invention can be used in many applications from coupling agents, to adhesion promoters, to polymers which can be cured by ultraviolet radiation, to heat curable compositions, to compositions which can be cured by electron beam radiation, as well as other radiation. One of the advantages of the acryl functional silicon compounds of this invention is that the compounds do not need to contain by-products which are undesirable for optical uses, for electrical uses, for heat stability uses where the presence of by-products or unreacted catalysts would cause degradation of the properties.

The silanes of this invention are useful as adhesion promoters or precursors which can be used to make other siloxane polymers by the use of mild hydrolysis. Such silanes can be of the following general formula

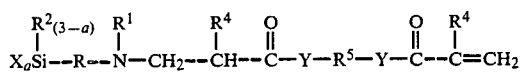

wherein

R is a divalent hydrocarbon radical, a divalent hydrocarbon radical having amino functionality of the formula $=NH$ in which the two bonds of the $=NH$ are bonded to carbon atoms, or a divalent hydrocarbon radical having amino functionality of the formula $=NH$ in which the two bonds of the $=NH$ are bonded to carbon atoms, and where the hydrogen of the $=NH$ is substituted with an acryl functional group of the general formula

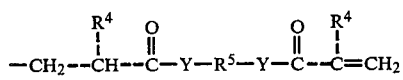

$R^1$ is hydrogen, an alkyl radical having from 1 to 4 carbon atoms per radical, or an acryl functional radical of the general formula

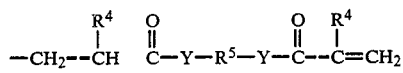

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical or divalent hydrocarbon radicals containing ether linkages, Y is a divalent oxygen atom or $-NR^1-$, a is 1, 2, or 3.

$R^5$ is a divalent hydrocarbon radical, for example, methylene, ethylene, propylene, butylene, hexylene, decylene,

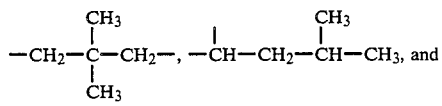

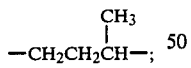

or a divalent hydrocarbon radical containing ether linkages, such as $-CH_2CH_2-O-CH_2CH_2-$, $-(CH_2CH_2O)_3-CH_2CH_2-$, $-(CH_2CH_2CH_2O)_{\overline{5}}-CH_2CH_2CH_{\overline{2}}-$, $-(CH_2CH_2O)_{\overline{8}}-CH_2CH_{\overline{2}}-$,

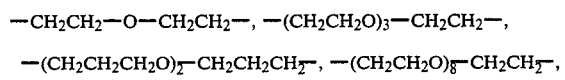

$-(CH_2CH_2CH_2CH_2O)_{7.8}-CH_2CH_2CH_2CH_2-$,

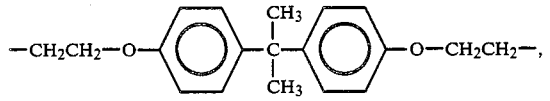 and 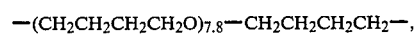.

Preferably, R is an alkylene radical of 3 to 10 carbon atoms or a radical of the formula $-CH_2CH_2CH_2-NH-CH_2CH_2-$, $R^2$ is methyl, X is $OR^3$ in which $R^3$ is an alkyl radical of from 1 to 8 carbon atoms or phenyl, $R^4$ is hydrogen, $R^5$ is a divalent hydrocarbon radical, Y is divalent oxygen atom, and a is 3.

The siloxanes of the present invention have at least one acryl functional group per molecule. These siloxanes can be used to make coating compositions which cure when exposed to ultraviolet radiation. Such coating compositions can be hard and resin like or they can be elastomeric or gel-like. Each of these find useful applications in the art, such as in electronic coatings, in optical fiber coating, and as paper coatings. The concentration of the acryl groups on the siloxane, the molecular weight of the siloxane, and the other organic groups on the siloxane can determine the final characteristics of the acryl functional silicon compound of this invention.

Acryl functional siloxanes of this invention which are preferred are polysiloxanes having at least one acryl functional siloxane unit of the general unit formula

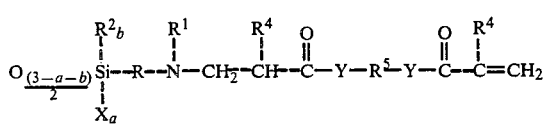

wherein

R is a divalent hydrocarbon radical, a divalent hydrocarbon radical having amino functionality of the formula $=NH$ in which the two bonds of the $=NH$ are bonded to carbon atoms, or a divalent hydrocarbon radical having amino functionality of the formula $=NH$ in which the two bonds of the $=NH$ are bonded to carbon atoms, and where the hydrogen of the $=NH$ is substituted with an acryl functional group of the general formula

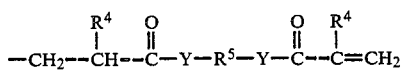

$R^1$ is hydrogen, an alkyl radical having from 1 to 4 carbon atoms per radical, an acryl functional radical of the general formula

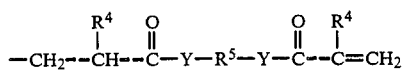

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical or divalent hydrocarbon radicals containing ether linkages, Y is a divalent oxygen atom or $-NR^1-$, a is 0, 1, or 2, b is 0, 1, or 2, and a+b is two or less, and any remaining siloxane units present in the polysiloxane are those having the general unit formula

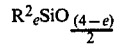

in which $R^2$ is defined above and e is 0, 1, 2, or 3.

One type of preferred siloxane containing acryl functionality is one in which there are two acryl functional siloxane units per molecule in which a is 0, b is 1 or 2, $R^2$ is methyl, R is

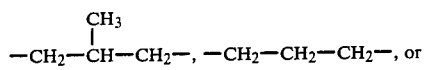

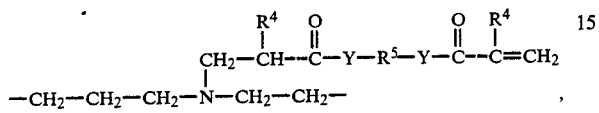

$R^1$ is methyl, $R^4$ is hydrogen atom, Y is divalent oxygen atom, $R^5$ is a divalent hydrocarbon radical of the general formula $-(CH_2)_d-$ in which d is an integer of from 1 to 6 and there is an average of 10 to 300 dimethylsiloxane units per molecule.

Another type of siloxane containing acryl functionality is one in which there are from 2 to 20 acryl functional siloxane units per molecule in which a is 0, b is 1, $R^2$ is methyl, R is

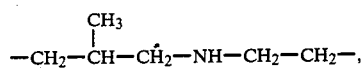

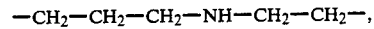

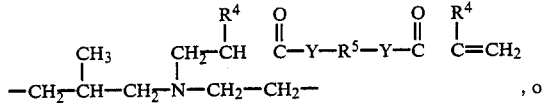

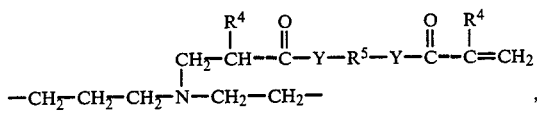

$R^1$ is hydrogen atom, $R^4$ is hydrogen atom, Y is divalent oxygen atom, $R^5$ is a divalent hydrocarbon radical of the general formula $-(CH_2)_d-$ in which d is an integer of from 1 to 6, there are two trimethylsiloxy units per molecule, and there is an average of from 100 to 500 dimethylsiloxane units per molecule.

A type of preferred silane containing acryl functionality and made using tri- or tetra-acryl functional acryl compounds has the following general formula

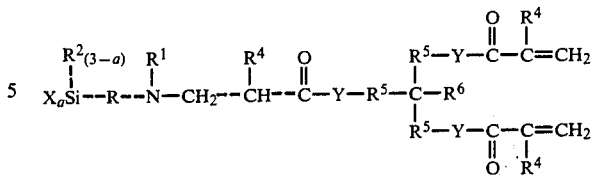

wherein

R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms and where the hydrogen of the =NH is substituted with an acryl functional group of the general formula

$R^1$ is hydrogen, an alkyl radical having from 1 to 4 carbon atoms per radical, or an acryl functional radical of the general formula

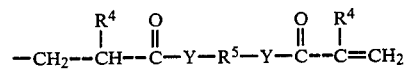

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical, divalent hydrocarbon radicals containing ether linkages, $R^6$ is a monovalent radical selected from the group consisting of a hydrocarbon radical, a hydroxyl substituted aliphatic hydrocarbon radical, and an acryl radical of the formula

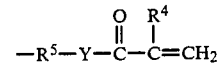

Y is a divalent oxygen atom or $-NR^1-$, a is 1, 2, or 3.

Siloxanes made from tri- or tetra-acryl functional compounds are those which have at least one siloxane unit of the following general unit formula

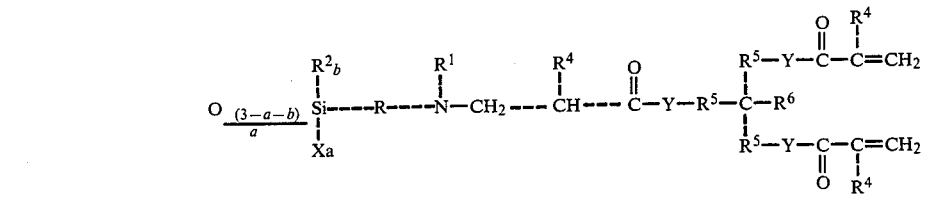

wherein
R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms, and where the hydrogen of the =NH is substituted with an acryl functional group of the general formula

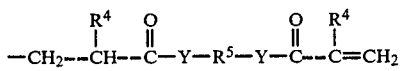

$R^1$ is hydrogen, an alkyl radical having from 1 to 4 carbon atoms per radical, or an acryl functional radical of the general formula

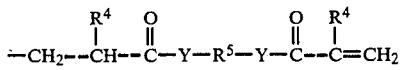

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical, divalent hydrocarbon radicals containing ether linkages, $R^6$ is a monovalent radical selected from the group consisting of a hydrocarbon radical, a hydroxyl substituted aliphatic hydrocarbon radical, and an acryl radical of the formula

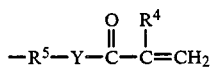

Y is a divalent oxygen atom —$NR^1$—, a is 0, 1, or 2, b is 0, 1, or 2, and a+b is two or less, and any remaining siloxane units present in the polysiloxane are those having the general unit formula

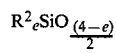

in which $R^2$ is defined above and e is 0, 1, 2, or 3.

The acryl functional siloxanes of this invention can be mixed with photoinitiator and then exposed to ultraviolet radiation to cause the siloxane to crosslink. The photoinitiator is used in amounts sufficient to provide the desired cure. Examples of photoinitiators include benzoin; benzoin alkyl ethers such as methyl, ethyl, isopropyl, and isobutyl benzion ethers; acetophenone derivatives, such as dialkoxyacetophenone exemplified by diethoxyacetophenone, dichloroacetophenone, trichloroacetophenone, alpha,alpha-dimethoxy-alpha-phenylacetophenone, 1-hydroxycyclohexylphenyl ketone, 2-hydroxy-2-methyl-1-phenylpropane-1-one, methylphenyl glyoxylate, 4-benzoylbenzyl-trimethylammonium chloride, alpha-acyloxime esters such as 1-phenyl-1,2-propanedione-2-(O-ethoxycarbonyloxime), benzophenone in combination with a chain transfer agent such as a NH group and azo-bis(isobutyronitrile), benzil ketals, and ketone amine derivatives. Polysilanes are useful in the compositions which are to be cured by ultraviolet radiation. The polysilane photoinitiators are those which have a chain of catenated silicon atoms in either a linear configuration or in a ring configuration. The polysilane are soluble in the acryl functional siloxanes. The polysilanes can be the phenylmethylpolysilanes defined by West in U.S. Pat. No. 4,260,780, issued Apr. 7, 1981 which is hereby incorporated by reference; the aminated methylpolysilanes defined by Baney et al. in U.S. Pat. No. 4,314,956, issued Feb. 9, 1982, which is hereby incorporated by reference; the methylpolysilanes of Peterson et al. in U.S. Pat. No. 4,276,424, issued June 30, 1981 which is hereby incorporated by reference; and the polysilastyrene defined by West et al. in U.S. Pat. No. 4,324,901, issued Apr. 13, 1982 which is hereby incorporated by reference.

The compositions of acryl functional siloxane and photoinitiator can contain a storage stabilizer which can be amines, particularly tertiary amines such as diisopropylaminoethanol and trioctylamine. Another type of viscosity stabilizer is the free radical scavenger type, such as p-methoxyphenol (also known as hydroquinone, catechol, 4-t-butylcatechol, phenothiazine, hydroquinone, 2,6-di-t-butyl-p-methylphenol, and N-phenyl-2-naphthylamine. The free radical scavenger viscosity stabilizers are used in amounts of preferably zero to one weight percent based on the weight of the composition. If free radical scavenger is used the amounts should be small such as from 0.01 to 0.1 weight percent.

Compositions of this invention which are crosslinked or cured can contain optional ingredients which may be suitable for some applications. Examples of these optional ingredients include surfactants, reinforcing agents such as fillers and resins, colorants, heat stabilizers and other property modifiers.

As stated above the compositions of this invention can be cured by other means which include exposure to electron beam radiation (does not require a photoinitiator), heating with peroxides and other methods which are known in the art to acryl functional compounds.

The following examples are present for illustrative purposes and should not be construed as limiting this invention which is properly delineated in the claims.

EXAMPLE 1

An acryl functional silicone was prepared by mixing 1,6-hexanediol diacrylate with an amine functional siloxane of the formula

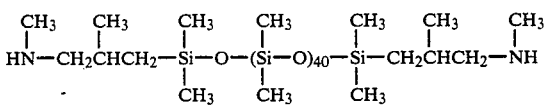

in a ratio of one mole of amine per one mole of diacrylate molecule. The mixture was heated to 70° C. and this temperature was maintained for 23 hours at which time 80% of the diacrylate had disappeared. The mixture was initially cloudy but turned clear during the reaction. A photoinitiator, Darocure ™ 1173 sold by E. M. Chemicals, in the amount of two weight percent was added to the reaction product. The reaction product is believed to have the formula

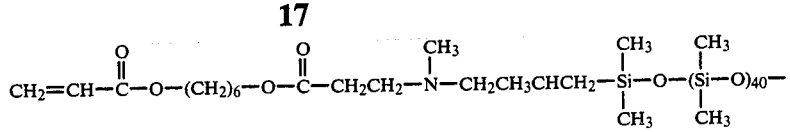

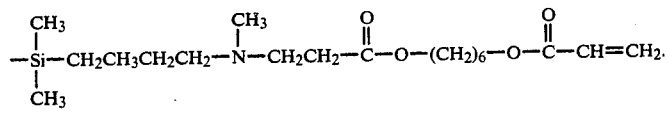

The Darocure 1173 has a formula

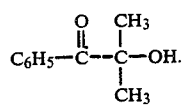

A film of the composition was cast and then exposed to ultraviolet radiation for 18 seconds. The resulting film had a tensile strength at break of 552 kilopascals with an elongation at break of 110%.

EXAMPLE 2

Acryl functional siloxane polymers were prepared by mixing the amounts shown in Table I into 10 g of an amine functional siloxane of the following average formula

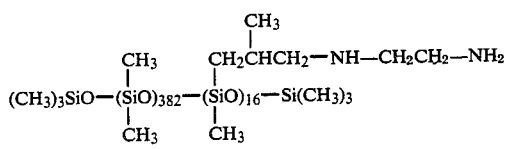

which is hereinafter referred to as Polymer A, or 10 g of an amine functional siloxane of the following average formula

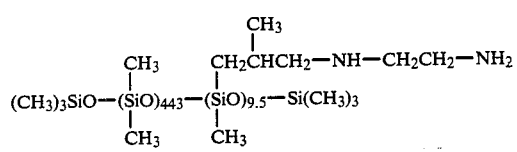

which is hereinafter referred to as Polymer B, and one acryl functional compound from the following formulae

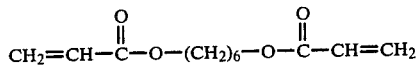

referred to as HDDA or

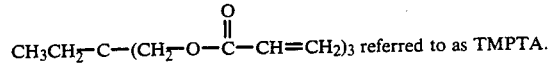

The mixtures were placed in capped vials and then heated in a convection oven at 70° C. The results were as shown in Table I. The mixtures were cloudy initially upon mixing the ingredients. These experiments show that the functionality of the amine containing silicon compound and the acryl functional compound need to be considered when making the acryl functional silicone compounds of this invention to ensure that the final products are those one wishes and can use. The shelf life of the reaction products in Table I were short but could be lengthened by adding either monofunctional acryl compound or an acid anhydride.

TABLE I

| RUN NO., POLYMER | TMPTA, GRAMS | HDDA, GRAMS | MOLES ACRYL COMPOUND/ MOLES AMINE HYDROGEN | COMMENTS |
| --- | --- | --- | --- | --- |
| 1,A | 4.55 | — | 1/1 | Medium gel formed in 10 minutes |
| 2,A | 1.52 | — | 1/3 | Hard gel formed in 10 minutes |
| 3,A | — | 3.47 | 1/1 | Clear in 30 minutes soft gel in 60 minutes |
| 4,A | — | 1.74 | 1/3 | Clear in 10 minutes gel in 30 to 60 min |
| 5,A | — | 3.47 | 1/1 | Clear in 45 minutes soft gel in 60 min |
| 6,A | — | 5.21 | 1.5/1 | Cloudy, viscous after 60 minutes gelled on cooling |
| 7,B | — | 2.48 | 1.5/1 | Opaque after 60 minutes gelled in 2 days |

The reaction products of Run No. 5 and Run No. 7 were mixed with two weight percent of Darocure ™ 1173 and two weight percent of diisopropylaminoethanol, cast on aluminum Q-panels in a thickness of 8 mils, and then exposed to ultraviolet radiation. The compositions cured to elastomeric but weak films. The dry cured film using the reaction product of Run No. 5 had a cured film thickness of 5 mils and a tensile strength at break of 1165 kilopascals and an elongation at break of 21%. The modulus at 2.5% was 145 kilopascals and at 5% was 296 kilopascals.

Run No. 5 was repeated except the ingredients were mixed and heated for 20 minutes at 70° C. and then p-methoxyphenol in amounts of 150 ppm and 500 ppm and ethylhexyl acrylate in an amount of 1.73 g per 10 g of the reaction product were added to separate portions.

In each case, the reaction product gelled within 24 hours. The free radical scavenger was not sufficient to achieve long shelf stability and the monofunctional acryl compound was neither enough or it was added to late during the reaction process. The following example will show that the monofuctional compound can be used to increase the shelf stability of the reaction product. Also the presence of excess multi-functional acryl compound can be used to add shelf stability to the final reaction product.

EXAMPLE 3

An acryl functional silicone compound was prepared by mixing 25 g of Polymer A and 8.68 g of HDDA (1 mole HDDA per 1 mole amine hydrogen) and then heating at 70° C. for 30 minutes at which time the mixture turned clear. The reaction product is hereinafter referred to as Product A.

A second acryl functional silicone compound was prepared by mixing 20 g of Polymer A and 13.88 g of HDDA (2 moles HDDA per 1 mole amine hydrogen) and then heating at 70° C. for 30 minutes at which time the mixture was still cloudy. The reaction product is hereinafter referred to as Product B.

Products A and B were mixed with various amounts of ethylhexyl acrylate (EHA) and HDDA and then the shelf life was observed to determine the concentration of the acryl compounds which would exhibit increased shelf life before gelling occurred. The amounts of the acryl compounds added and the results of the shelf life observed are shown in Table II.

The tensile strength at break, the elongation at break, and the modulus were measured on compositions made by mixing the reaction products with two weight percent Darocure ™ 1173 and two weight percent diisopropylaminoethanol, casting a film of about 8 mils thick on aluminum Q-panels, and then exposing the castings to ultraviolet radiation. The cured films had thicknesses of about 5 mils. The results were as shown in Table III.

TABLE II

| RUN NO., PRODUCT | GRAMS PRODUCT | EHA, GRAMS | OBSERVATION |
| --- | --- | --- | --- |
| 8,A | 10 | 0.0 | Clear, gelled in <1 hour |
| 9,A | 9 | 1.0 | Clear, gelled in ca. 1 hour |
| 10,A | 7 | 3.0 | Clear, gelled in ca. 20 hours |
| 11,B | 10 | 0.0 | Cloudy, gelled in ca. 2.25 hours |
| 12,B | 9 | 1.0 | Clear, gelled in ca. 20 hours |
| 13,B | 7 | 3.0 | Clear, fluid after 20 hours, gelled in ca. 2 days |

TABLE III

| COMPOSITION | PRODUCT FROM RUN NO. | TENSILE, kPa | ELONGATION, % | MODULUS, kPa AT 2.5% | AT 5% |
| --- | --- | --- | --- | --- | --- |
| 14 | 11 | 2020 | 13 | 427 | 862 |
| 15 | 12 | 2848 | 18 | 469 | 938 |
| 16 | 13 | 1634 | 19 | 234 | 462 |

EXAMPLE 4

Acryl functional siloxane polymers were prepared by mixing 10 g of Polymer A with 5.21 g of HDDA. This mixture was opaque initially. Without any additives, this mixture formed a reaction product which was a cloudy gel in about 2.5 hours at room temperature. Ethanol was added to another sample of this mixture in the amount of 1.52 g, and this mixture formed a clear reaction product which gelled in about 40 minutes at room temperature. Another mixture was prepared by mixing Polymer A and HDDA as described above with 1.52 g of toluene, which formed a clear reaction product at room temperature which gelled between 2.5 and 24 hours. A fourth mixture was prepared by combining Polymer A and HDDA with 1.52 g of isopropyl alcohol. This mixture formed a clear reaction product which gelled in about 2.5 hours. In every case, heating the reaction resulted in a clear gel. The addition of ethanol and isopropyl alcohol increased the rate of the reaction as indicated by the rapid formation of a clear reaction product.

The reaction product is believed to be a siloxane polymer of the structure of Polymer A in which the amine hydrogens are reacted with HDDA and in which the following siloxane units are present, namely trimethylsiloxy units, dimethylsiloxane units,

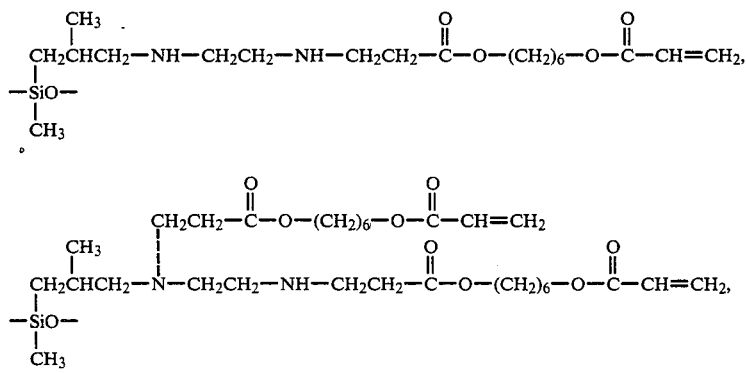

-continued

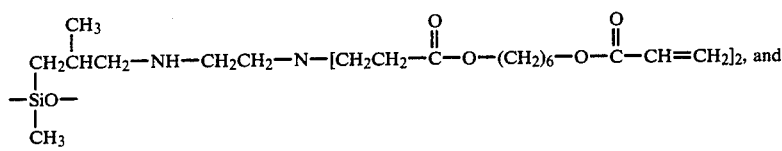

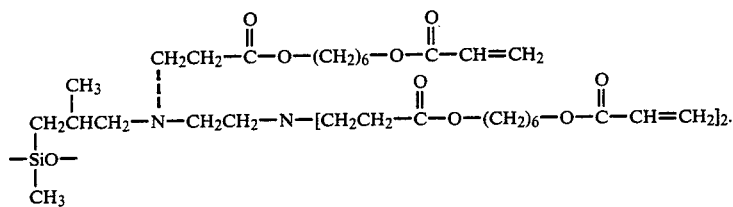

These siloxane units are randomly distributed along the polymer chain.

EXAMPLE 5

Two acryl functional siloxane polymers were prepared by mixing 7 g of an amine functional polymer of the following formula

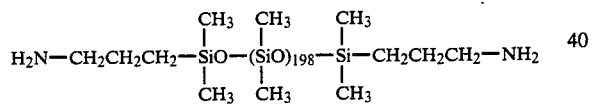

which is hereinafter referred to as Polymer C, 0.63 g of HDDA, 0.37 g of ethanol, and 0.019 cc of a 1% solution of p-methoxyphenol. One of these mixtures was mixed and maintained at room temperature and after 60 minutes the mixture was still cloudy but more viscous. This reaction product is referred to as Product C. The other mixture was mixed and was initially cloudy but after heating at 60° C. for 15 minutes the mixture became clear and remained clear after 60 minutes of heating but became cloudy upon cooling to room temperature. This reaction product is referred to as Product D. A third mixture was prepared as described above in this example except that 0.74 g of ethanol was used instead of the 0.37 g. This mixture was mixed and maintained at room temperature. It was somewhat cloudy initially but became clear after 60 minutes. This reaction product is referred to as product E. To each of the reaction products, 3.0 g of isobornyl acrylate and 0.2 g of Darocure ™ 1173 was added. Each of the reaction products became clear fluids which had a viscosity at 25° C. in the range of 0.5 to 1.0 Pa.s and a shelf life of >4 days. Films of these compositions were deposited and then exposed to ultraviolet radiation while under a blanket of nitrogen gas. The cured films had the properties shown in Table IV and were elastomeric.

TABLE IV

| PRODUCT | TENSILE STRENGTH, kPa | ELONGATION, % | MODULUS kPa, AT 2.5% |
|---|---|---|---|
| C | 1965 | 102 | 593 |
| D | 2772 | 133 | 669 |
| E | 2717 | 120 | 717 |

The reaction products are believed to have the following endblocking siloxane units

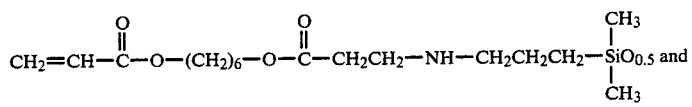

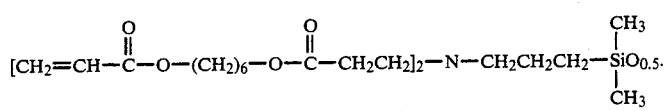

and

It is also believed that there would be endblocking units in which the isobornyl acrylate reacted with the amine hydrogen atoms which had not yet reacted with HDDA at the time the isobornyl acrylate was added.

EXAMPLE 6

Acryl functional silane was prepared by mixing at room temperature 0.64 g of an amine silane of the formula

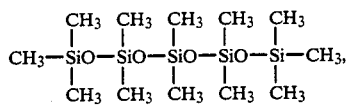

0.37 g of HDDA, 3.0 g of siloxane as solvent of the formula

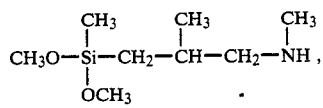

0.5 g of the following siloxane as an internal standard for the gas chromatogram

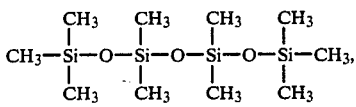

and 0.5 g of the solvents shown in Table V to show whether the solvent has an effect on the reaction rate, i.e. a promoter solvent. Also shown in Table V is the percentage disappearance of the amine and the HDDA which was an indication of the completion of the reaction.

TABLE V

| SOLVENT | REACTION TIME | PERCENT DISAPPEARANCE | |
|---|---|---|---|
| | | AMINE | HDDA |
| ISOPROPYL ALCOHOL | 0 min | 0.0 | 0.0 |
| | 32 min | 6.6 | 8.8 |
| | 68 min | 16.6 | 23.0 |
| | 114 min | 26.4 | 35.8 |
| | 71 hours | 99.3 | 100.0 |
| $CH_3-Si(CH_3)_2-O-(Si(CH_3)_2-O)_3-Si(CH_3)_3$ | | | |
| | 0 min | 0.0 | 0.0 |
| | 35 min | 3.1 | 3.1 |
| | 109 min | 8.0 | 7.1 |
| | 19 hours | 27.6 | 44.9 |
| | 67 hours | 46.0 | 75.7 |
| TOLUENE | 0 min | 0.0 | 0.0 |
| | 67.5 hours | 41.6 | 69.8 |

The reaction product of these reactions is believed to be silanes of the following formula

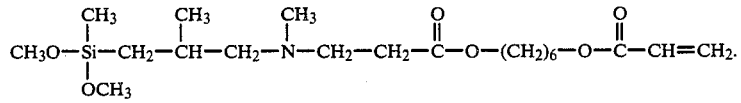

The reaction of the amine silane and the HDDA shows that the alcohol greatly increases the rate of the reaction.

That which is claimed is:

1. An acryl functional silicone compound consisting essentially of at least one silicon atom having an acryl functional radical bonded to the silicon atom through a silicon-carbon bond, where the acryl functional radical contains at least one carbon-nitrogen-carbon bond and an acrylate, methacrylate, acrylamide, or methacrylamide group, any other groups bonded to the silicon atom being monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together, silicon atoms which are present and which do not have an acryl functional radical bonded thereto can have bonded thereto monovalent hydrocarbon radicals, fluorinated alkyl radicals, hydrolyzable groups whose hydrolyzed groups do not form a salt with the nitrogen atoms, divalent oxygen atoms which bond radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together, silicon atoms which are present and which do not have an acryl functional radical bonded thereto can have bonded thereto monovalent hydrocarbon radicals, fluorinated alkyl radicals, hydrolyzable groups whose hydrolyzed groups do not form a salt with the nitrogen atoms, divalent oxygen atoms which bond two silicon atoms in an Si—O—Si linkage, divalent hydrocarbon radicals bonding at least two silicon atoms together.

2. The acryl functional silicone compound according to claim 1 in which the compound is a silane having the following formula

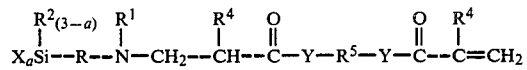

wherein

R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms, and where the hydrogen of the =NH is substituted with an acryl functional group of the general formula

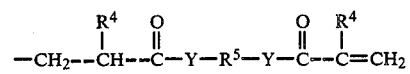

$R^1$ is hydrogen, an alkyl radical having from 1 to 4 carbon atoms per radical, or an acryl functional radical of the general formula

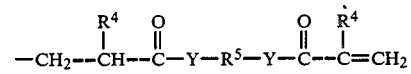

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical or divalent hydrocarbon radicals containing ether linkages, Y is a divalent oxygen atom or $-NR^1-$, a is 1, 2, or 3.

3. The acryl functional silicone compound according to claim 2 in which R is an alkylene radical having from 3 to 10 carbon atoms per radical, $R^2$ is methyl, X is $OR^3$ in which $R^3$ is an alkyl radical of from 1 to 8 carbon radicals per radical or phenyl, $R^4$ is a hydrogen atom, $R^5$ is a divalent hydrocarbon radical, Y is a divalent oxygen atom, and a is 3.

4. The acryl functional silicone compound according to claim 1 in which the compound is a polysiloxane having at lest one acryl functional siloxane unit of the general unit formula $$\underset{\underline{2}}{O_{(3-a-b)}} \overset{R^2_b}{\underset{X_a}{\overset{|}{Si}}} - R - \overset{R^1}{\underset{|}{N}} - CH_2 - \overset{R^4}{\underset{|}{CH}} - \overset{O}{\underset{||}{C}} - Y - R^5 - Y - \overset{O}{\underset{||}{C}} - \overset{R^4}{\underset{|}{C}} = CH_2$$

wherein

R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms, and where the hydrogen of the =NH is substituted with an acryl functional group of the general formula $$-CH_2 - \overset{R^4}{\underset{|}{CH}} - \overset{O}{\underset{||}{C}} - Y - R^5 - Y - \overset{O}{\underset{||}{C}} - \overset{R^4}{\underset{|}{C}} = CH_2$$

$R^1$ is hydrogen, an alkyl radical having from 1 to 4 carbon atoms per radical, an acryl functional radical of the general formula $$-CH_2 - \overset{R^4}{\underset{|}{CH}} - \overset{O}{\underset{||}{C}} - Y - R^5 - Y - \overset{O}{\underset{||}{C}} - \overset{R^4}{\underset{|}{C}} = CH_2.$$

$R^2$ is a monovalent hydrocarbon radical or fluorinated alkyl radical,
X is a hydrolyzable group whose hydrolyzed groups do not form salts with the nitrogen atom,
$R^4$ is a hydrogen atom or a methyl radical,
$R^5$ is a divalent hydrocarbon radical or divalent hydrocarbon radicals containing ether linkages,
Y is a divalent oxygen atom or $-NR^1-$,
a is 0, 1, or 2,
b is 0, 1, or 2, and
a+b is two or less, and
any remaining siloxane units present in the polysiloxane are those having the general unit formula $$R^2_e SiO_{\frac{(4-e)}{2}}$$

in which $R^2$ is defined above and e is 0, 1, 2, or 3.

5. The polysiloxane according to claim 4 in which there are two acryl functional siloxane units per molecule in which a is 0, b is 2, $R^2$ is methyl, R is $$-CH_2-\overset{CH_3}{\underset{|}{CH}}-CH_2-,$$

$R^1$ is methyl, $R^4$ is hydrogen atom, Y is divalent oxygen atom, $R^5$ is a divalent hydrocarbon radical of the general formula $-(CH_2)_d-$ in which d is an integer of from 1 to 6 and there is an average of 10 to 300 dimethylsiloxane units per molecule.

6. The polysiloxane according to claim 4 in which there are from 2 to 20 acryl functional siloxane units per molecule in which a is 0, b is 1, $R^2$ is methyl, R is $$-CH_2-\overset{CH_3}{\underset{|}{CH}}-CH_2-NH-CH_2-CH_2-$$

$R^1$ is hydrogen atom, $R^4$ is hydrogen atom, Y is divalent oxygen atom, $R^5$ is a divalent hydrogen radical of the general formula $-(CH_2)_d-$ in which d is an integer of from 1 to 6, there are two trimethylsiloxy units per molecule, and there is an average of from 100 to 500 dimethylsiloxane units per molecule.

7. The polysiloxane according to claim 4 in which there are two acryl functional siloxane units per molecule in which a is 0, b is 2, $R^2$ is methyl, R is $$-CH_2-CH_2-CH_2-\underset{|}{N}-CH_2-CH_2-\underset{|}{\overset{CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2,}{}}$$

$R^1$ is methyl, $R^4$ is hydrogen atom, Y is divalent oxygen atom, $R^5$ is a divalent hydrocarbon radical of the general formula $-(CH_2)_d-$ in which d is an integer of from 1 to 6 and there is and average of 10 to 300 dimethylsiloxane units per molecule.

8. The polysiloxane according to claim 4 in which there are from 2 to 20 acryl functional siloxane units per molecule in which a is 0, b is 1, $R^2$ is methyl, R is $$-CH_2-CH_2-CH_2-\underset{|}{N}-CH_2-CH_2-\underset{|}{\overset{CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2,}{}}$$

$R^1$ is hydrogen atom, $R^4$ is hydrogen atom, Y is divalent oxygen atom, $R^5$ is a divalent hydrocarbon radical of the general formula $-(CH_2)_d-$ in which d is an integer of from 1 to 6, there are two trimethylsiloxy units per molecule, and there is an average of from 100 to 500 dimethylsiloxane units per molecule.

9. The polysiloxane according to claim 4 in which there are two acryl functional siloxane units per molecule in which a is 0, b is 2, $R^2$ is methyl, R is $-CH_2-CH_2-CH_2-$, $R^1$ is methyl, $R^4$ is hydrogen atom, Y is divalent oxygen atom, $R^5$ is a divalent hydrocarbon radical of the general formula $-(CH_2)_d-$ in which d is an integer of from 1 to 6 and there is an average of 10 to 300 dimethylsiloxane units per molecule.

10. The acryl functional silicone compound according to claim 1 in which the compound is a silane having the following general formula $$\overset{R^2_{(3-a)}}{\underset{X_a}{\overset{|}{Si}}} - R - \overset{R^1}{\underset{|}{N}} - CH_2 - \overset{R^4}{\underset{|}{CH}} - \overset{O}{\underset{||}{C}} - Y - R^5 - \overset{R^5-Y-\overset{O}{\underset{||}{C}}-\overset{R^4}{\underset{|}{C}}=CH_2}{\underset{R^5-Y-\underset{||}{\overset{C}{\underset{O}{-}}}-\underset{|}{\overset{C}{\underset{R^4}{=}}}CH_2}{\overset{|}{C}-R^6}}$$

wherein

R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms, and where the hydrogen of the =NH is substituted with an acryl functional group of the general formula $$-CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2$$

$R^1$ is hydrogen, an alkyl radical having from 1 to 4 carbon atoms per radical, or an acryl functional radical of the general formula $$-CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2$$

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical or divalent hydrocarbon radicals containing ether linkages, $R^6$ is a monovalent radical selected from the group consisting of a hydrocarbon radical, a hydroxyl substituted aliphatic hydrocarbon radical, and an acryl radical of the formula $$-R^5-Y-\overset{O}{\underset{||}{C}}-\overset{R^4}{\underset{|}{C}}=CH_2$$

Y is a divalent oxygen atom or $-NR^1-$, a is 1, 2, or 3.

11. The acryl functional silicone compound according to claim 1 in which the compound is a siloxane having at least one unit of the following general unit formula $$O_{\frac{(3-a-b)}{a}}\overset{R^2_b}{\underset{\underset{X_a}{|}}{Si}}-R-\overset{R^1}{\underset{|}{N}}-CH_2-\overset{R^4}{\underset{|}{CH}}-\overset{O}{\underset{||}{C}}-Y-R^5-\overset{R^5-Y-\overset{O}{\underset{||}{C}}-\overset{R^4}{\underset{|}{C}}=CH_2}{\underset{R^5-Y-\underset{||}{C}-\underset{|}{C}=CH_2}{\underset{O\ R^4}{|}}}{\underset{|}{C}}-R^6$$

wherein

R is a divalent hydrocarbon radical, a divalent hydrocarbon radical having amino functionality of the formula =NH in which the two bonds of the =NH are bonded to carbon atoms, or a divalent hydrocarbon radical having amino functionality of the formula =NH in which the two bonds of the =NH are bonded to carbon atoms, and where the hydrogen of the =NH is substituted with an acryl functional group of the general formula $$-CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2$$

$R^1$ is hydrogen, an alkyl radical having from 1 to 4 carbon atoms per radical, or an acryl functional radical of the general formula $$-CH_2-\overset{R^4}{\underset{|}{CH}}-\overset{O}{\underset{||}{C}}-Y-R^5-Y-\overset{O}{\underset{||}{C}}-\overset{R^4}{\underset{|}{C}}=CH_2$$

$R^2$ is a monovalent hydrocarbon radical or fluorinated alkyl radical,

X is a hydrolyzable group whose hydrolyzed groups do not form salts with the nitrogen atom, $R^4$ is a hydrogen atom or a methyl radical, $R^5$ is a divalent hydrocarbon radical or divalent hydrocarbon radicals containing ether linkages, $R^6$ is a monovalent radical selected from the group consisting of a hydrocarbon radical, a hydroxyl substituted aliphatic hydrocarbon radical, and an acryl radical of the formula $$-R^5-Y-\overset{O}{\underset{||}{C}}-\overset{R^4}{\underset{|}{C}}=CH_2$$

Y is a divalent oxygen atom or $-NR^1-$, a is 0, 1, or 2, b is 0, 1, or 2, and a+b is two or less, and any remaining siloxane units present in the polysiloxane are those having the general unit formula $$R^2_eSiO_{\frac{(4-e)}{2}}$$

in which $R^2$ is defined above and e is 0, 1, 2, or 3.

12. The polysiloxane according to claim 11 in which there are from 2 to 20 acryl functional siloxane units in which a is 0, b is 1, R is $$-CH_2-\overset{CH_3}{\underset{|}{CH}}-CH_2-NH-CH_2-CH_2-$$

$R^1$ is hydrogen atom, $R^4$ is hydrogen atom, Y is divalent oxygen atom, $R^5$ is a divalent hydrocarbon radical of the general formula $-(CH_2)_d-$ in which d is an integer of from 1 to 6, and $R^6$ is ethyl, there are two trimethylsiloxy units per molecule, and there is an average of from 100 to 500 dimethylsiloxane units per molecule.

13. A method of preparing an acryl functional silicone compound comprising forming an intimate mixture of an amino functional silicon compound in which the amino group is a primary amine or a secondary amine and an acryl functional compound having at least two acrylate, methacrylate, acrylamide, or methacrylamide groups per molecule at a temperature less than 100° C. for a time sufficient to produce an acryl functional silicone compound in which at least one silicon atom having an acryl functional radical bonded to the silicon atom through a silicon-carbon bond, where the acryl functional radical contains at least one carbonnitrogen-carbon bond and an acrylate, methacrylate, acrylamide, or methacrylamide group, any other groups bonded to the silicon atom being monovalent hydrocarbon two silicon atoms in an Si—O—Si linkage, divalent hydrocarbon radicals bonding at least two silicon atoms together.

14. The method according to claim 13 in which the intimate mixture is heated to a temperature above 25° C. but not exceeding 100° C.

15. The method according to claim 13 further comprising a promoter solvent in the mixture.

16. The method according to claim 14 further comprising a promoter solvent in the mixture.

17. The method according to claim 15 in which the promoter solvent is an alcohol.

18. The method according to claim 13 further comprising the presence of a monofunctional acrylate or methacrylate in the reacting mixture to stop the reaction and to extend the shelf life of the resultant acryl functional silicone.

19. An acryl functional silicone compound obtained from the method of claim 13.

20. An acryl functional silicone compound obtained from the method of claim 15.

21. An acryl functional silicone compound obtained from the method of claim 17.

22. An acryl functional silicone compound obtained from the method of claim 18.

23. The method according to claim 14 further comprising a free radical scavenger.

24. An acryl functional silicone compound obtained from the method of claim 23.

25. The method in accordance with claim 13 further comprising adding to the resultant product an acid anhydride which reacts with available =NH groups in the acryl functional silicone compound to produce the following group

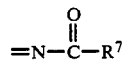

wherein $R^7$ is a monovalent hydrocarbon radical or a radical of the general formula —$R^8$—COOH in which $R^8$ is a divalent hydrocarbon radical.

26. An acryl functional silicone compound obtained from the method of claim 25.

* * * * *